US010105165B2

(12) United States Patent
Biedermann et al.

(10) Patent No.: US 10,105,165 B2
(45) Date of Patent: Oct. 23, 2018

(54) INSTRUMENT FOR HOLDING AND INSERTING A BONE ANCHOR

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Timo Biedermann, Trossingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 652 days.

(21) Appl. No.: 14/645,307

(22) Filed: Mar. 11, 2015

(65) Prior Publication Data
US 2015/0257797 A1  Sep. 17, 2015

Related U.S. Application Data

(60) Provisional application No. 61/953,548, filed on Mar. 14, 2014.

(30) Foreign Application Priority Data

Mar. 14, 2014 (EP) .................................... 14160107

(51) Int. Cl.
*A61B 17/86* (2006.01)
*A61B 17/70* (2006.01)
*A61B 17/88* (2006.01)

(52) U.S. Cl.
CPC ...... *A61B 17/7082* (2013.01); *A61B 17/7001* (2013.01); *A61B 17/8891* (2013.01); *A61B 17/861* (2013.01)

(58) Field of Classification Search
CPC ............ A61B 17/7091; A61B 17/7001; A61B 17/8605; A61B 17/861; A61B 17/8891; A61B 17/8888; A61B 17/8886
See application file for complete search history.

(56) References Cited

U.S. PATENT DOCUMENTS 4,763,548 A     8/1988 Leibinger et al.
5,649,931 A *   7/1997 Bryant ............... A61B 17/8891
                                              606/104

(Continued)

FOREIGN PATENT DOCUMENTS

DE   20 2005 012 781 U1   11/2005

OTHER PUBLICATIONS

European Search Report; Application Serial No. 14160107.0; dated Sep. 18, 2014; Completion Date Sep. 9, 2014; 7 Sheets.

*Primary Examiner* — Brian Dukert
(74) *Attorney, Agent, or Firm* — Lewis Roca Rothgerber Christie LLP

(57) ABSTRACT

An instrument for holding and inserting a bone anchor into a bone is provided, where the bone anchor includes a shank for anchoring in the bone and a head. The instrument includes a holding member for holding the head of the bone anchor and has a plurality of arms configured to at least partially encompass the head, where the arms include an inner surface forming a seat for the head. The instrument also includes a drive shaft for engaging the head of the bone anchor and defining a longitudinal axis of the instrument. The instrument further includes a displacement member configured to act on the holding member. The holding member can assume a first configuration in which it is configured to permit the head to enter the seat and a second configuration in which it is configured to hold the head in the seat.

21 Claims, 10 Drawing Sheets

(56) References Cited

U.S. PATENT DOCUMENTS

| | | | | |
|---|---|---|---|---|
| 5,667,513 A | * | 9/1997 | Torrie | ............... A61B 17/0401 606/104 |
| 6,189,422 B1 | | 2/2001 | Stihl | |
| 2012/0296171 A1 | | 11/2012 | Lovell et al. | |

* cited by examiner

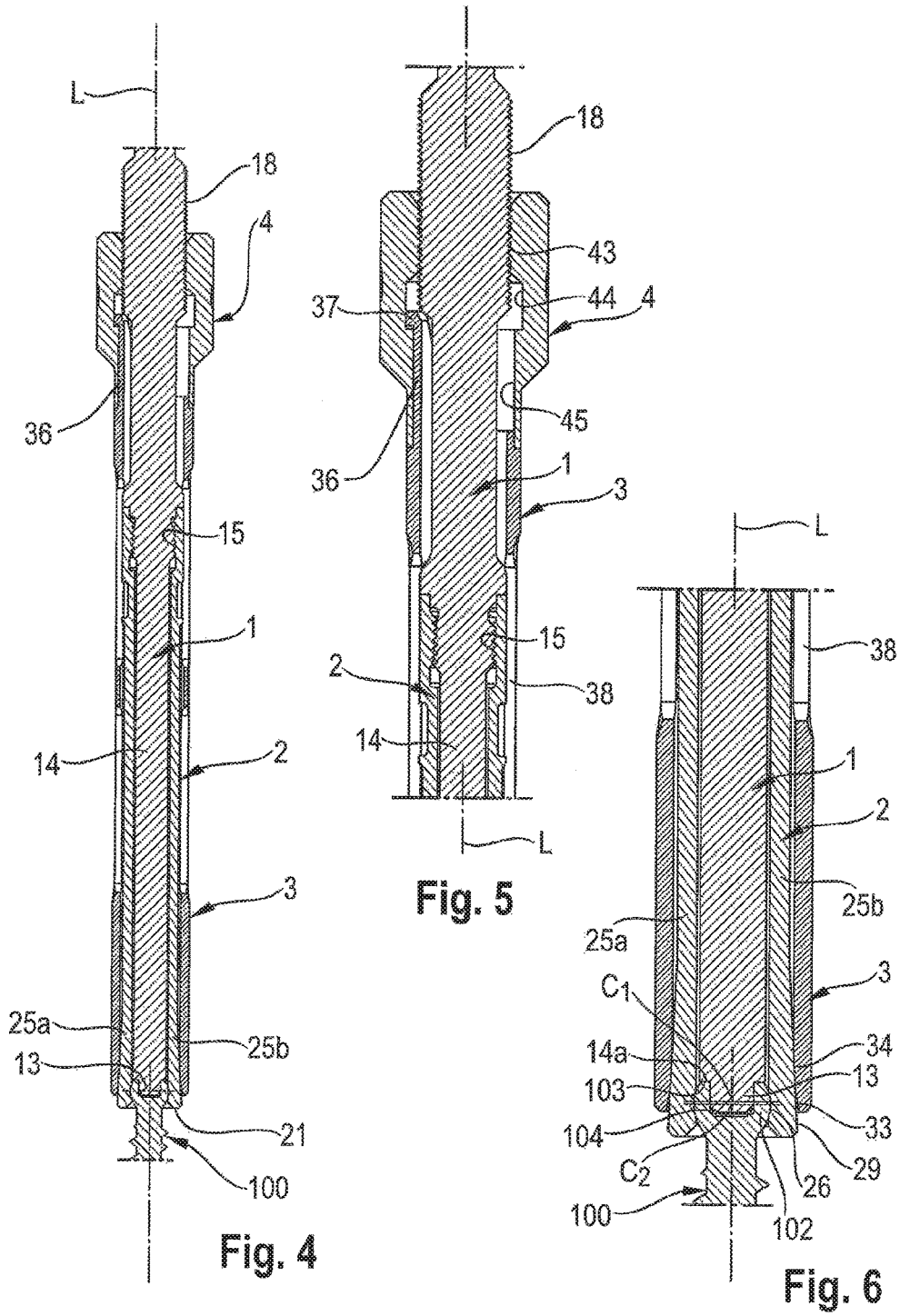

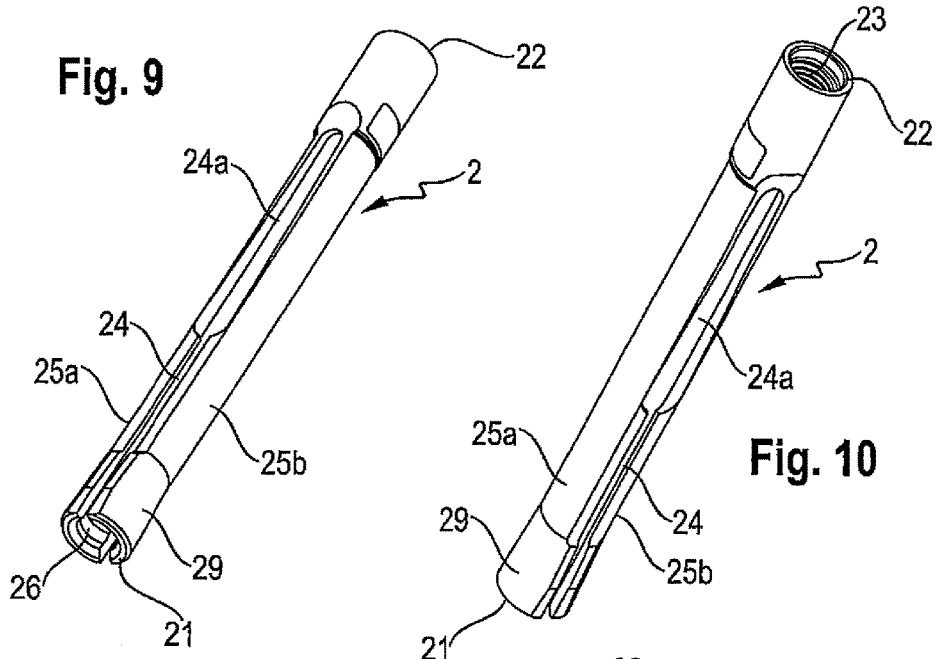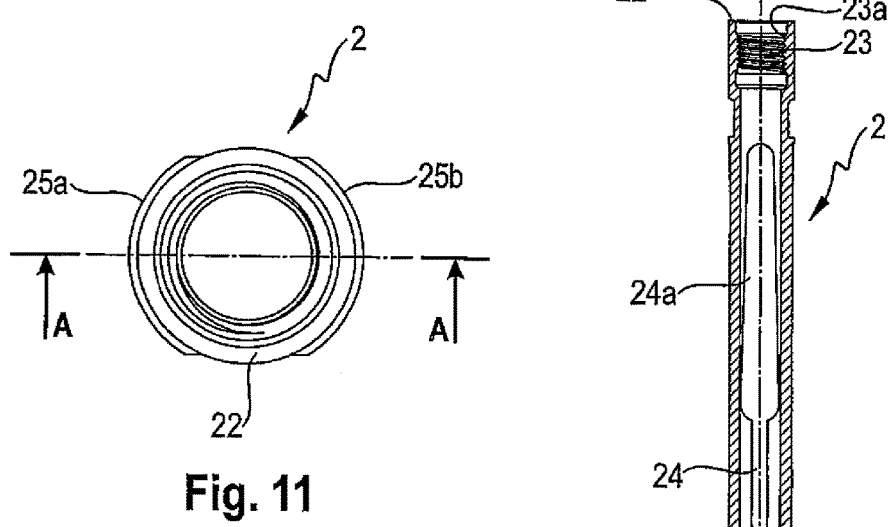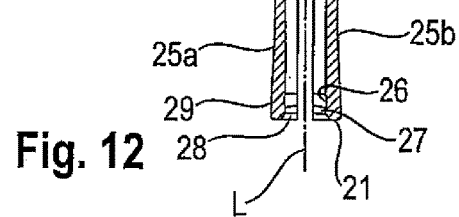

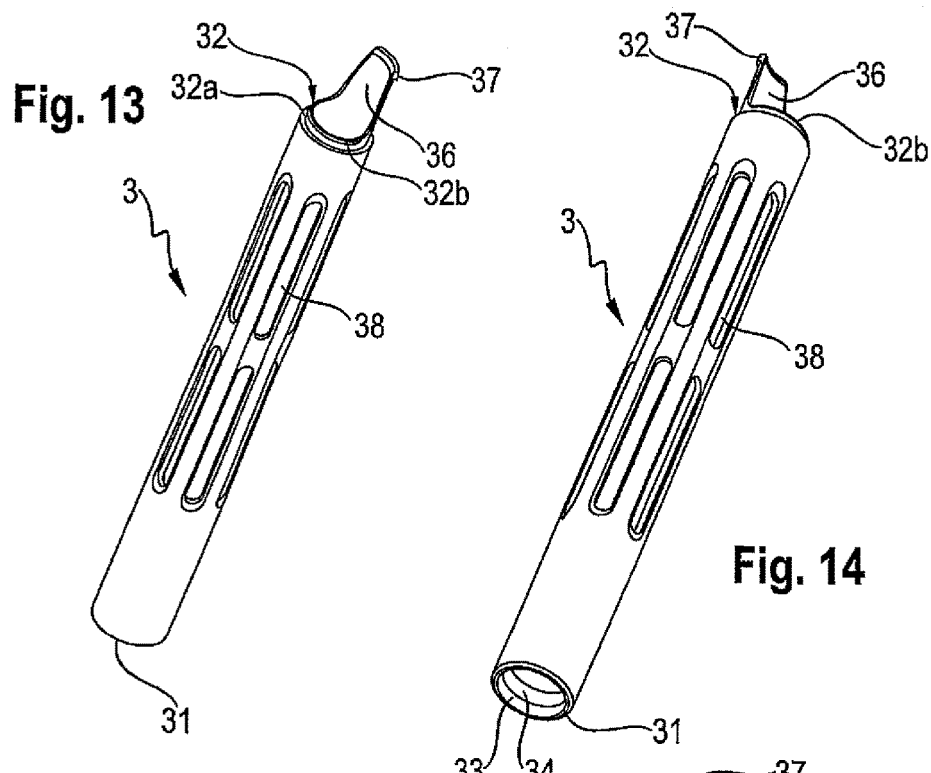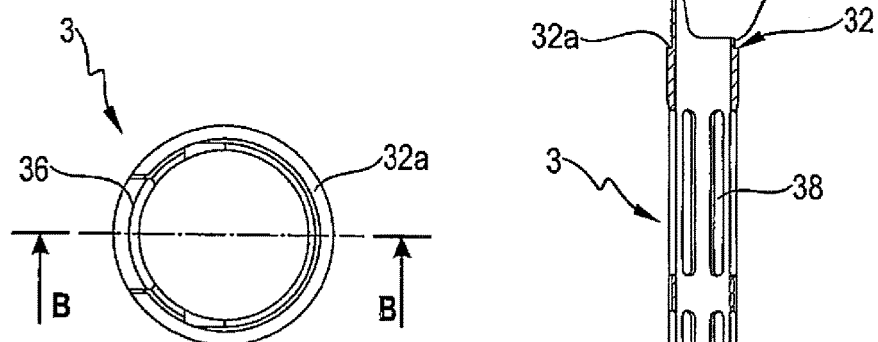

INSTRUMENT FOR HOLDING AND INSERTING A BONE ANCHOR

CROSS-REFERENCE TO RELATED APPLICATIONS

The present disclosure claims the benefit of U.S. Provisional Patent Application Ser. No. 61/953,548, filed on Mar. 14, 2014, the contents of which are hereby incorporated by reference in their entirety, and claims priority to European Patent Application EP 14160107.0, filed on Mar. 14, 2014, the contents of which are hereby incorporated by reference in their entirety.

BACKGROUND

Field of the Invention

The present disclosure relates to an instrument for holding and inserting a bone anchor into a bone. The instrument includes a holding member including at least two arms that are configured to hold a head of the bone anchor between them. The instrument also includes a displacement member that acts on the holding member such that the holding member can assume a first configuration in which the holding member is configured to receive the head, and a second configuration in which the holding member holds an inserted head. Further, the instrument includes a drive shaft that is configured to engage the head of the bone anchor. The instrument may be used with a polyaxial bone anchoring device of a bottom loading type that has a bone anchor and a receiving part to receive a rod to connect the rod to the bone anchor, where the bone anchor is first inserted into the bone using the instrument and the receiving part is mounted in situ onto the bone anchor thereafter.

Description of the Related Art

An instrument for holding and inserting of bone screws, in particular of pedicle screws, is known from DE 20 2005 012 781 U1. The instrument includes a holding member with at least two gripping arms for a bone screw and a displacement member that is movable relative to the gripping arms. By means of the displacement member, the gripping arms can assume a configuration which allows the insertion of the bone anchor and a configuration in which the bone anchor is held between the arms. The gripping arms have projections that engage recesses on the bone screw to allow the screwing-in of the bone screw via the gripping arms.

US 2012/0296171 A1 describes an inserter for a bone anchor including a driver for engaging the head of a bone screw and a receiver member with a spherical inner surface portion that becomes engaged with the head and/or the neck of the bone anchor.

SUMMARY

Embodiments of the invention provide an instrument for holding and inserting a bone anchor that provides a safe and robust connection between the bone anchor and the instrument and an automatic alignment of the bone anchor and the instrument.

The instrument includes a holding member with a seat for a head of a bone anchor. The instrument also includes a displacement member for acting on the holding member such that the holding member can assume a first configuration in which the holding member permits the head to enter or be inserted into the seat, and a second configuration in which the holding member holds the inserted head. The instrument further has a drive shaft configured to engage the head of the bone anchor. A center of the seat of the holding member can be offset from a center of the head such that the head is pressed against an abutment surface of the drive shaft when the head is inserted into the holding member. Thereby, play between an engagement portion of the drive shaft and the head is eliminated. This allows a precise insertion of the bone anchor into a bone without experiencing play between the drive shaft and the bone anchor. Also, by means of this design, the connection between the instrument and the bone anchor is robust.

The head of the bone anchor may be held in the seat in a form-fit or positive-fit manner. Furthermore, the drive shaft of the instrument may include an engagement portion that engages a corresponding engagement portion of the head of the bone anchor in a form-fit manner. Thereby, the bone anchor can be automatically aligned correctly with the drive shaft.

The size and position of the seat may be designed such that a lower end of the holding member acts as an abutment for a bone surface. Hence, when the bone anchor is inserted into a bone with the instrument, the free lower end of the holding member can abut against the bone surface to indicate that a correct insertion of the bone anchor has been reached to allow for easier in situ mounting of a receiving part to the bone anchor thereafter.

BRIEF DESCRIPTION OF THE DRAWINGS

Further features and advantages of the invention will become apparent from the description of embodiments by means of the accompanying drawings. In the drawings:

FIG. 4 shows a cross-sectional view of a portion of the instrument of FIGS. 1 to 3, the cross-section taken in a plane containing a longitudinal axis of the instrument;

FIG. 5 shows an enlarged cross-sectional view of an upper portion of the instrument of FIG. 4;

FIG. 6 shows an enlarged cross-sectional view of a lower portion of the instrument of FIG. 4;

FIG. 9 shows a perspective view from a front end of a holding member of the instrument of FIGS. 1 to 6;

FIG. 10 shows a perspective view from a rear end of the holding member shown in FIG. 9;

FIG. 11 shows a top view of the rear end of the holding member of FIGS. 9 and 10;

FIG. 12 shows a cross-sectional view of the holding member of FIGS. 9 to 11, the cross-section taken along line A-A in FIG. 11.

FIG. 13 shows a perspective view from a rear end of a displacement member of the instrument of FIGS. 1 to 6;

FIG. 14 shows a perspective view from a front end of the displacement member of FIG. 13;

FIG. 15 shows a top view of the rear end of the displacement member of FIGS. 13 and 14;

FIG. 16 shows a cross-sectional view of the displacement member of FIGS. 13 to 15, the cross-section taken along line B-B in FIG. 15;

FIG. 23b shows an enlarged cross-sectional view of a detail of FIG. 23a; and

DETAILED DESCRIPTION

Figure 1:
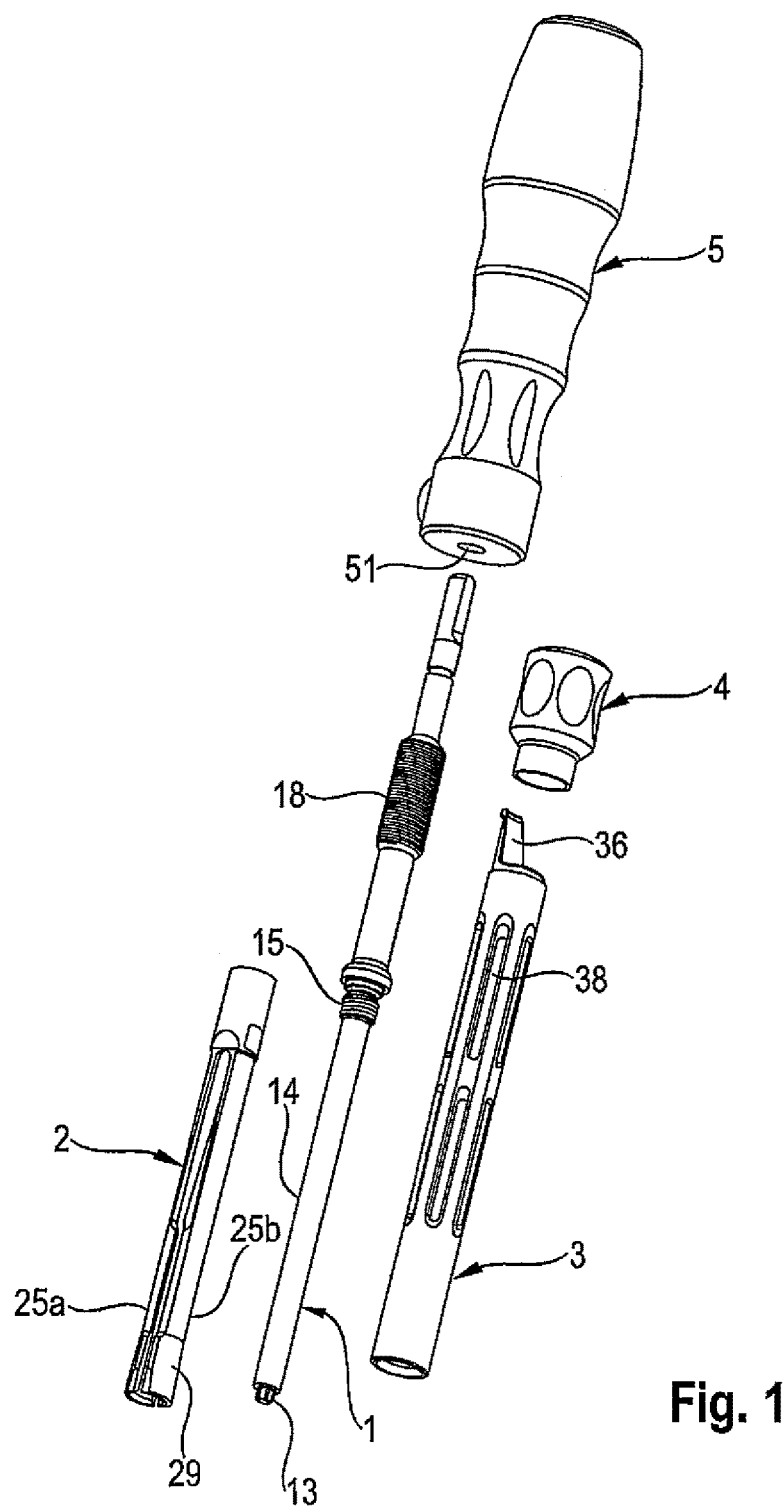
FIG. 1 shows an exploded perspective view of an instrument according to an embodiment of the invention.
Figures 2, 3:
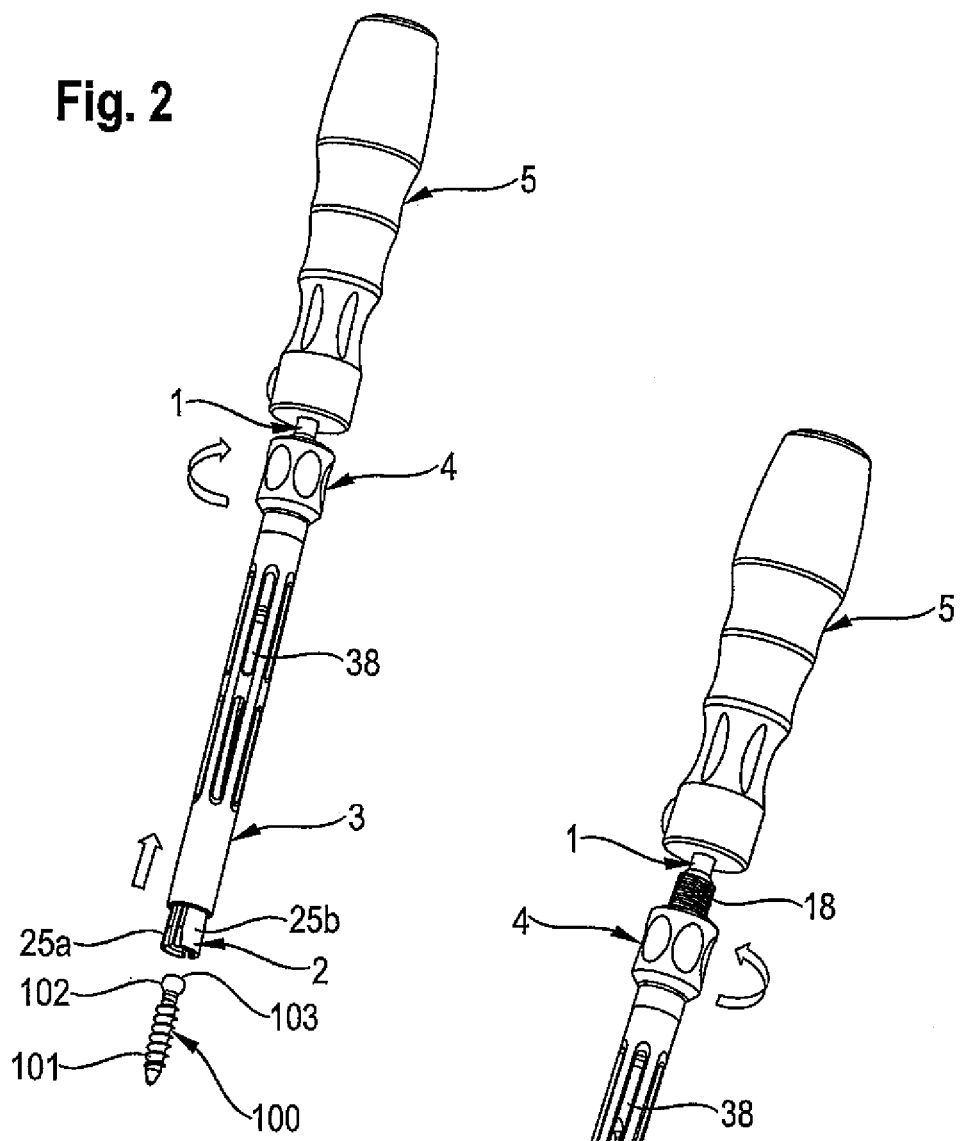
FIG. 2 shows a perspective view of the instrument of FIG. 1 in an assembled state in a first configuration where the instrument is configured to receive a head of a bone anchor.
FIG. 3 shows a perspective view of the instrument of FIGS. 1 and 2 in a second configuration where the head of the bone anchor is received and clamped by the instrument.
Figure 7:
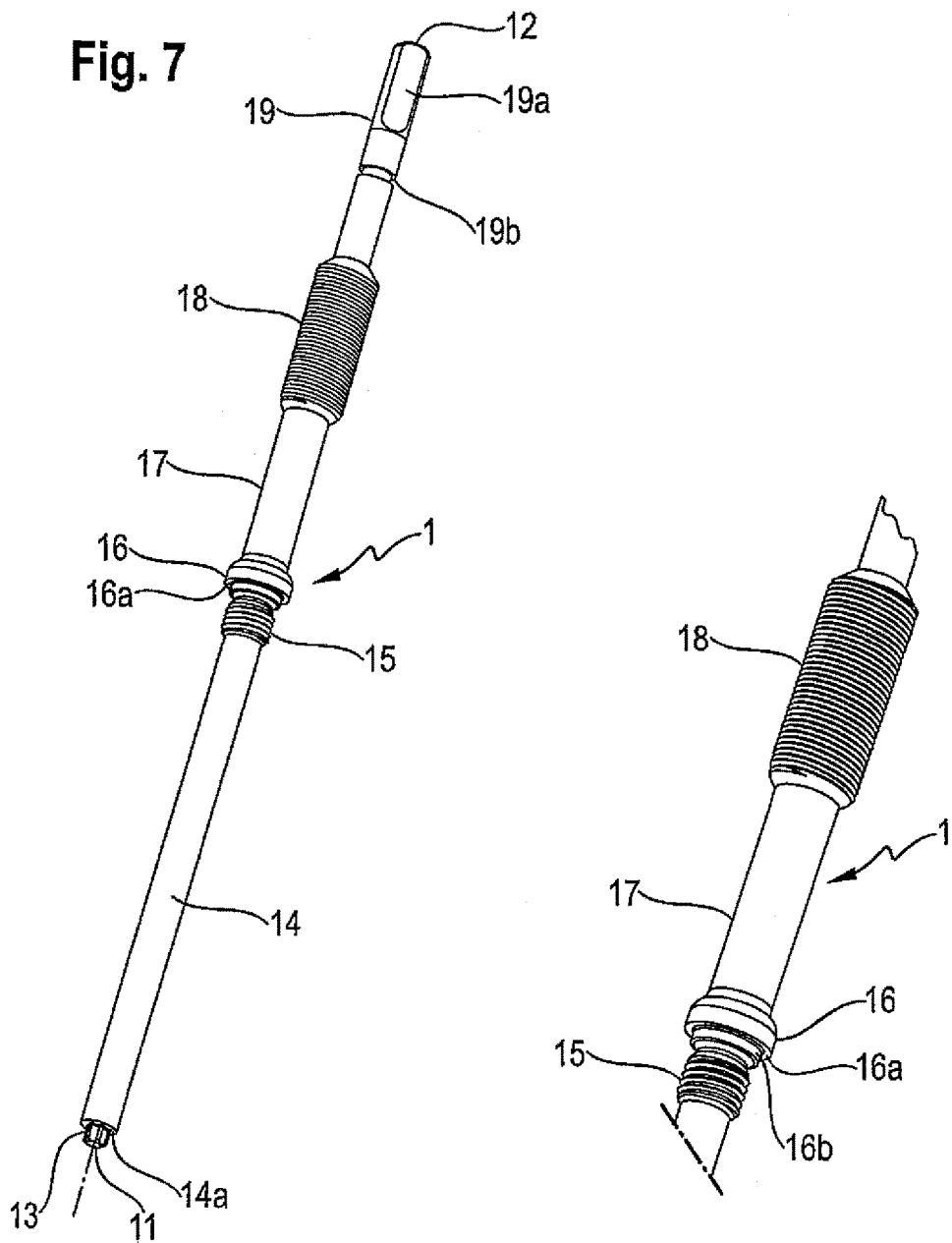
FIG. 7 shows a perspective view of a drive shaft of the instrument of FIGS. 1 to 6.
Figure 8:
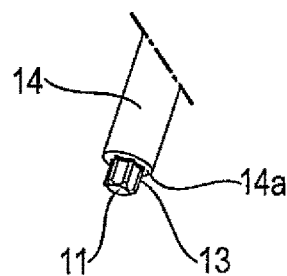
FIG. 8 shows enlarged views of two portions of the drive shaft of FIG. 7.
Figure 17:
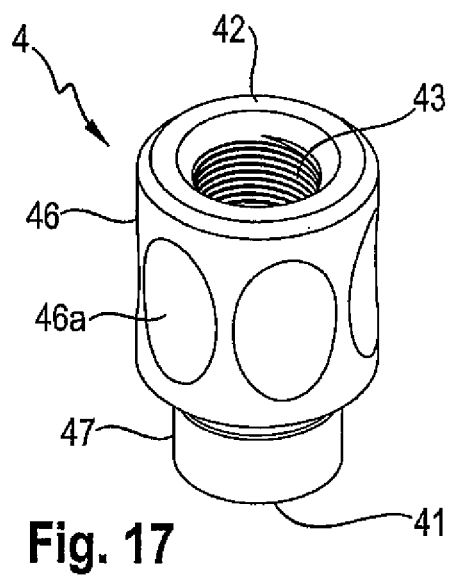
FIG. 17 shows a perspective view from a rear end of an actuator of the instrument according to FIGS. 1 to 6.
Figure 18:
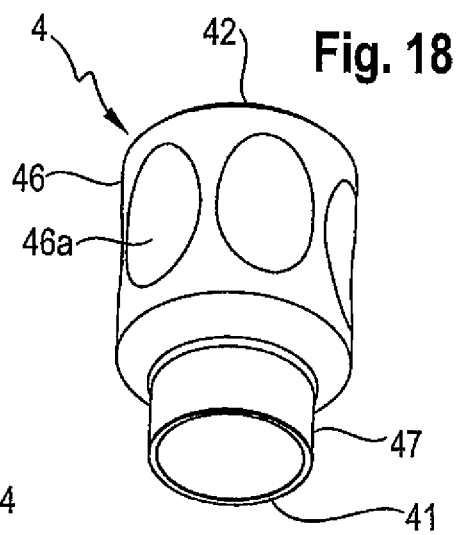
FIG. 18 shows a perspective view from a front end of the actuator of FIG. 17.
Figure 19:
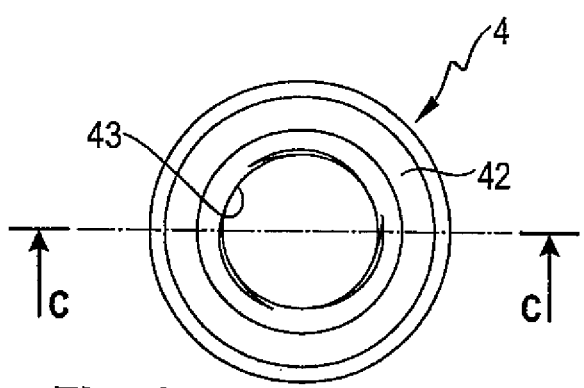
FIG. 19 shows a top view from of the rear end of the actuator of FIGS. 17 and 18.
Figure 20:
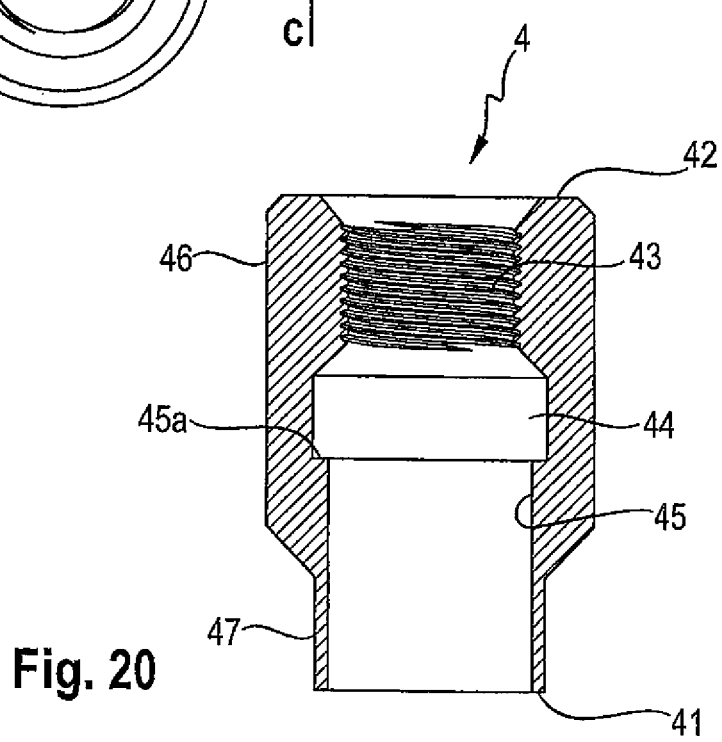
FIG. 20 shows a cross-sectional view of the actuator of FIGS. 17 to 19, the cross-section taken along line C-C in FIG. 19.

Referring to FIGS. 1 to 3, an instrument for holding and inserting a bone anchor into a bone according to an embodiment of the invention includes a drive shaft 1 that is configured to engage a head portion of the bone anchor and to transmit torque to the bone anchor. The instrument also includes a holding member 2 for receiving and holding the head of the bone anchor and a displacement member 3 that is configured to act on the holding member 2. The holding member can assume a first configuration as depicted in FIG. 2, where the head of the bone anchor can be inserted into the holding member, and a second configuration as depicted in FIG. 3, where the head of the bone anchor is firmly held in the holding member 2. The instrument further includes an actuator 4 that cooperates with the drive shaft 1 and the displacement member 3 to move the displacement member 3 into first and second positions corresponding to the first and second configurations of the holding member 2. The instrument also includes a handle 5 that is connectable to the drive shaft 1.

Referring to FIGS. 2 and 3, a bone anchor 100 in this embodiment includes a threaded shank 101 and a head 102 at one end of the threaded shank 101. The head 102 may have a surface portion that is spherically-shaped and a substantially flat free end surface 103. The spherical surface portion may include a region spanning a greatest diameter of the sphere. The bone anchor may be used in polyaxial bone anchoring devices that can be used for stabilization of the spinal column by means of stabilizing rods. The polyaxial bone anchoring devices may have a receiving part (not shown) that is configured to pivotably receive the bone anchor 100 and to receive the spinal stabilization rod (not shown) to couple the rod to the bone anchor. The instrument may be used with bottom loading type polyaxial bone anchoring devices where the head 102 of the bone anchor 100 is inserted into the receiving part from a bottom end thereof (i.e., from an end of the receiving part that faces the bone surface).

With reference to FIGS. 4 to 8, the drive shaft 1 may be a monolithic substantially rod-shaped member that has a first end or distal end 11 and an opposite second end or proximal end 12. At the first end 11, an engagement projection 13 is provided that is configured to engage a corresponding recess in the head 102 of the bone anchor 100 to transmit torque to the head 102. In the embodiment shown, the engagement projection 13 has a TORX™-shape. However, any other shape is possible that allows connecting the engagement projection 13 to the head 102 of the bone anchor 100 in a form-fit or positive-fit manner. Following the engagement projection 13, the drive shaft 1 includes a first shaft portion 14 with a first diameter that is greater than the diameter of the engagement projection 13. At a front end of the first shaft portion 14 nearest the engagement projection 13, an abutment surface 14a is formed that extends circumferentially around the engagement projection 13 and that is substantially flat.

At a side of the first shaft portion 14 opposite to the engagement projection 13, the first shaft portion 14 has a threaded section 15 with an outer thread that cooperates with a corresponding inner thread of the holding member 2 and that allows the holding member 2 to be mounted onto the first shaft portion 14. At a distance from the threaded section 15, a section 16 with a larger outer diameter than the threaded section 15 is provided, which forms an annular abutment surface 16a facing towards the first end 11 of the drive shaft 1. The abutment surface 16a functions as a stop for the holding member 2 when the holding member is mounted to the first shaft portion 14. An intermediate portion 16b with a slightly smaller diameter than the section 16 may be present to improve the stability and/or the alignment of the connection between the holding member 2 and the drive shaft 1.

Between the second end 12 and the larger diameter section 16, there is a second shaft portion 17 that includes a portion 18 with a greater outer diameter that is located approximately at a middle region of the second shaft portion 17 between the second end 12 and the section 16. The portion 18 is threaded and cooperates with the actuator 4. The thread of the portion 18 may be a fine pitch thread and more particularly, may be a multi-start fine pitch thread, such as a double-start fine pitch thread. This makes it possible to obtain a greater displacement of the displacement member 3 and the actuator 4 in an axial direction of the actuator 4, for example, compared to using a single-start thread, when the actuator 4 is screwed back and forth along the threaded portion 18. Hence, the displacement of the displacement member 3 can be achieved with less turns or in shorter time. An end section 19 of the drive shaft 1 adjacent to the second end 12 has one or more longitudinal flats 19a to provide a form-fit connection to the handle 5, such that the handle 5 cannot rotate relative to the drive shaft 1 once the handle 5 is mounted to the drive shaft 1. An annular groove 19b at the end section 19 may be provided that cooperates with a corresponding projection in the handle 5 to prevent inadvertent separation of the handle 5 from the drive shaft 1.

A longitudinal axis L of the instrument is defined by the cylindrical drive shaft 1.

Next, the holding member 2 will be explained with reference to FIGS. 9 to 12. The holding member 2 is sleeve-shaped and has a first end or distal end 21 and an opposite second end or proximal end 22. At a distance from the second end 22, an internally threaded section 23 is provided with a slightly smaller inner diameter than that of the holding member 2 at the second end 22. The internally threaded section 23 cooperates with the threaded section 15 of the drive shaft 1. A shoulder 23a is formed by the reduction of the inner diameter of the holding member 2 that faces towards the second end 22 and that cooperates with the intermediate portion 16b of the drive shaft 1. The holding member 2 includes a slot 24 that is open to the first end 21 and that extends transversely through the holding member 2 in a plane including the longitudinal axis L such that two resilient arms 25a, 25b are formed by the slot 24. The slot 24 widens into a substantially elongate opening 24a that is closed near the second end 22. The opening 24a provides greater flexibility to the arms 25a, 25b.

At a distance from the first end 21, there is an inner spherical segment-shaped section that provides a seat 26 for the head 102 of the bone anchor 100. A radius of the inner spherical segment-shaped section 26 substantially matches the shape of an outer surface portion of the head 102. As can be seen in detail in FIG. 23b, a region with a largest diameter of the sphere defined by the spherical-segment shaped section 26 is between an upper edge 26a and a lower edge 26b of the seat 26. Hence, when the head 102 is received in the seat 26 and the arms 25a, 25b are pressed together, the head 102 is held in a form-fit manner in the seat 26. Adjacent to the seat 26, a cylindrical section 27 is provided with an inner diameter that is smaller than an inner diameter of the lower edge 26b of the seat 26 (see also FIG. 23b). Between the cylindrical section 27 and the first end 21, there is a tapered section 28 that tapers and narrows towards the seat 26. When the head 102 is received in the seat 26 and the arms 25a, 25b are pressed together, the head 102 is held in the holding member 2 such that the head 102 cannot be removed through the first end 21 of the holding member 2.

Figure 23A:
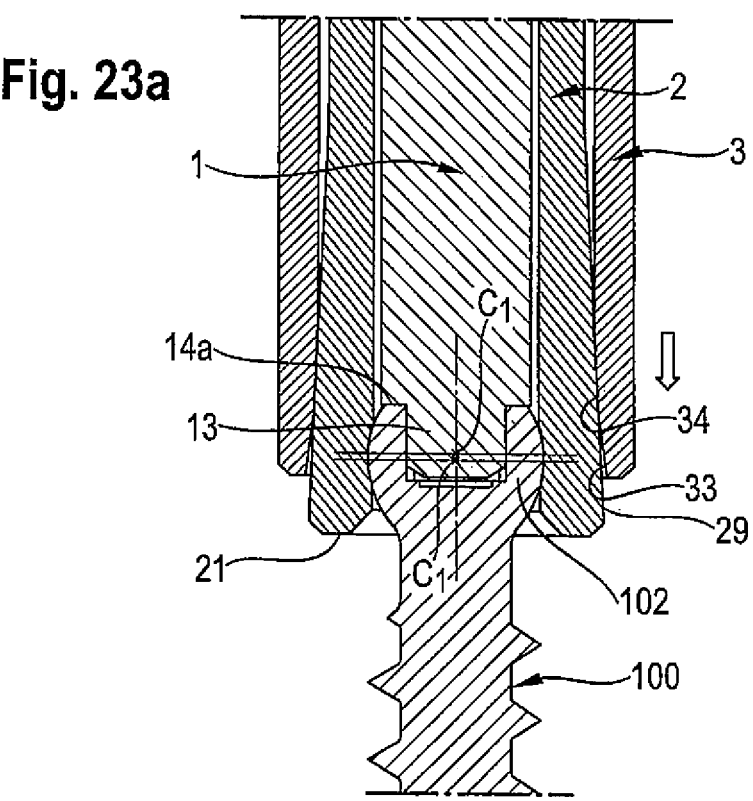
FIG. 23a shows a cross-sectional view of the instrument of FIGS. 1 to 6 in the second configuration with the head of the bone anchor inserted therein.
Figure 23B:
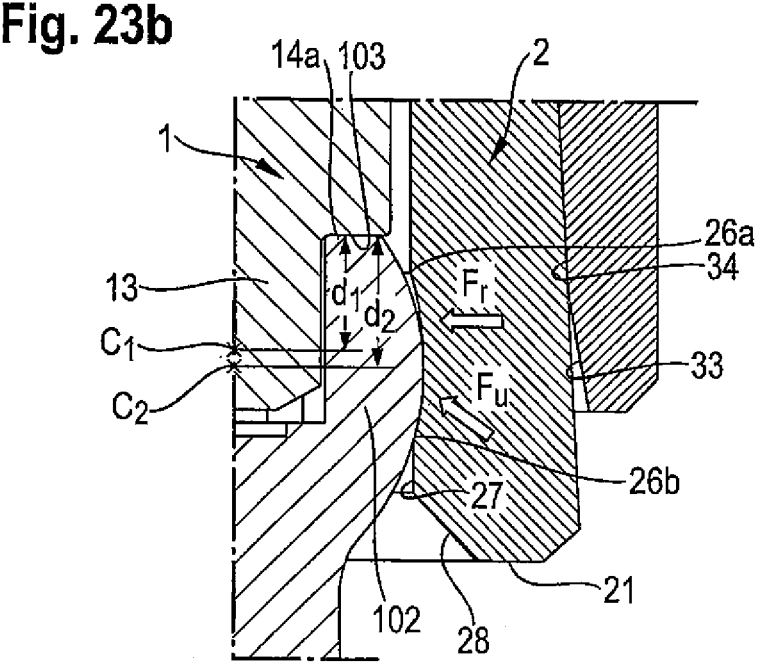

Referring more in detail to FIGS. 6 and 23b, when the head 102 is held in the seat 26, the center of the sphere $C_1$ of the seat 26 is offset in an axial direction from the center of the sphere $C_2$ of the head 102. More specifically, in this second configuration of the holding member 2, an axial distance $d_1$ from the center of the sphere of the seat 26 to the abutment surface 14a of the drive shaft 1 is smaller than an axial distance $d_2$ from the center of the sphere $C_2$ of the head 102 to the abutment surface 14a. By means of this, when the head 102 is held in the seat 26, the head 102 experiences a force that tends to move the head 102 towards the abutment surface 14a.

The dimensions of the lower portion of the holding member 2, that includes the seat 26, the cylindrical portion 27 and the tapered portion 28, may, for example, correspond substantially to a receiving part of a polyaxial bone anchoring device or may be slightly larger in an axial direction. Therefore, when the head 102 is held in the holding member 2 and inserted into the bone, the first end 21 of the holding member 2 forms an abutment for the bone surface such that the bone anchor 100 is inhibited from further insertion into the bone. At this position, the head 102 protrudes above the bone surface to such an extent that the receiving part can be easily mounted thereon.

A length of the holding member 2 is such that when the holding member 2 is screwed onto the threaded section 15 of the drive shaft 1 until the second end 22 of the holding member 2 abuts against the abutment surface 16a, the first end 21 of the holding member 2 extends beyond the first end 11 of the drive shaft 1 by a distance. This distance is such that the offset between the centers of the spheres $C_1$ and $C_2$ of the seat 26 and the head 102, respectively, causes the free end surface 103 of the head 102 to be pressed against the abutment surface 14a of the drive shaft 1. An inner diameter of the holding member 2 is such that the first portion 14 of the drive shaft 1 can pass therethrough and is guided therein.

Furthermore, as depicted in particular in FIG. 12, an outer surface portion 29 of the holding member 2 adjacent to the first end 21 of the holding member 2 is tapered such that the outer surface portion 29 narrows towards the second end 22. Hence, the holding member 2 may resemble and function like a collet chuck.

The displacement member 3 will be described with reference to FIGS. 4 to 6 and 13 to 16. The displacement member 3 is formed as a substantially cylindrical sleeve with a first end or distal end 31 and an opposite second end or proximal end 32. An inner diameter of the displacement member 3 is such that, as can be seen in FIGS. 4 to 6, the holding member 2 can extend through the displacement member 3. Adjacent to the first end 31, an inner surface section 33 of the displacement member 3 is slightly tapered such that the displacement member 3 widens towards the first end 31. In the direction towards the second end 32, the slightly tapered section 33 is followed by a second slightly tapered section 34 that tapers at an angle that is smaller than an angle of the taper of the first tapered section 33. The remaining portions of the displacement member 3 have a cylindrical inner surface 35. The function of the slightly tapered surface sections 34 and 33 are to cooperate with the tapered outer surface portion 29 of the holding member 2 when the displacement member 3 is moved from a first position in the first configuration to a second position in the second configuration. During this displacement, the tapered inner surface sections 34 and 33 slide along the tapered outer surface portion 29, thereby generating an increasing pressure onto the arms 25a, 25b that presses the arms together to clamp an inserted head 102.

The second end 32 of the displacement member 3 has a free annular end surface 32a that acts as an abutment for the actuator 4 as described below. From the end surface 32a, a short circular rim 32b with a smaller inner diameter than the annular end surface 32a protrudes upward away from other portions of the displacement member 3. Moreover, a flap-like extension or flap 36 projects above the rim 32b. The flap 36 has a substantially cylindrical inner surface, a substantially cylindrical outer surface, and a trapezoidal contour when viewed from the side. A width of the flap 36 adjacent to the rim 32b is larger than a width of a free end of the flap 36. Furthermore, at the free end, the flap 36 includes an outwardly extending circumferential projection 37 that cooperates with a portion of the actuator 4, to be described below. The height of the flap 36 between the end surface 32a and the outward projection 37 corresponds substantially to the height of an inner portion of the actuator 4 in an axial direction. The flap 36 has the function of a follower that allows rotation between the displacement member 3 and the actuator 4, but prevents axial movement of the displacement member 3 relative to the actuator 4. Therefore, axial advancement of the actuator 4 results in a corresponding axial advancement of the displacement member 3.

The displacement member 3 may further have a plurality of elongated openings 38 that extend completely through a cylindrical wall portion of the displacement member 3. The openings 38 facilitate the cleaning of the parts of the instrument.

A total axial length of the displacement member 3 is such that in a first position of the actuator 4 that corresponds to the first configuration, the first end 31 of the displacement member 3 has a distance from the first end 21 of the holding member 2 that allows the first end 21 of the holding member 2 to spread outward from the first end 31 of the displacement member 3 to facilitate insertion of the head 102. Furthermore, the axial length of the displacement member 3 is such that in a second position of the actuator 4 that corresponds to the second configuration, the tapered inner sections 33, 34 cooperate with the tapered outer surface portion 29 of the holding member to clamp the inserted head 102 in the holding member 2.

The actuator 4 will be described with reference to FIGS. 4 to 6 and 17 to 20. The actuator 4 includes a first end or distal end 41 and an opposite second or proximal end 42. At a small distance from the second end 42, a bore 43 with an internal thread is provided that cooperates with the external thread of the portion 18 of the drive shaft 1. In some embodiments, the internal thread may be a multi-start fine thread. Adjacent to the threaded bore 43, there is an inner substantially cylindrical section 44 that has a diameter that is greater than an outer diameter of the threaded portion 18 of the drive shaft 1 such that the threaded portion 18 of the drive shaft 1 can extend therethrough. Between the cylindrical inner section 44 and the first end 41, a second cylindrical section 45 is provided with a smaller diameter than the cylindrical section 44, such that an annular shoulder 45a is provided within the actuator 4. An inner diameter of the cylindrical section 45 is such that the second shaft portion 17 of the drive shaft 1 and the flap 36 of the displacement member 3 can extend therethrough, as can be seen in particular in FIG. 5. A distance between the shoulder 45a and the first end 41 is such that the flap 36 can abut against the shoulder 45a with a lower side of the circumferential outward projection 37 and the first end 41 of the actuator can abut against the free end surface 32a of the displacement member 3. Hence, the displacement member 3 is configured to be connected to the actuator 4 via the flap 36 such that the actuator 4 can rotate with respect to the displacement member 3, but the displacement member 3 is fixed against displacement in an axial direction with respect to the actuator 4.

The actuator 4 further includes an upper substantially cylindrical outer section 46 adjacent to the second end 42 with a plurality of flats 46a that facilitate gripping. The flats 46a are depicted as being oval-shaped, but can have any other shape. Any number of flats 46a can be implemented. In other embodiments, instead of the flats 46a, other means can be used to facilitate gripping, such as, for example, longitudinal ripples or grooves or a roughened surface.

The actuator further includes a second outer cylindrical section 47 adjacent to the first end 41, with an outer diameter that substantially corresponds to an outer diameter of the displacement member 3, such that the outer diameter of the actuator 4 can be flush with the outer diameter of the displacement member 3 as depicted in FIGS. 3 to 5.

Referring further to FIG. 1, the handle 5 includes a coaxial bore 51 that has an internal flat portion that cooperates with the flat 19a of the drive shaft, such that the handle 5 can be mounted onto the rear end portion 19 of the drive shaft 1 in a rotationally fixed manner. The bore 51 of the handle 5 may have an internal annular projection that engages the groove 19b of the drive shaft 1, such that the handle 5 may be secured (e.g., clicked) onto the drive shaft 1.

All parts of the instrument that may come into contact with tissue or bone may be made of a body-compatible material, such as, for example, stainless steel.

The instrument is easy to assemble and disassemble. Therefore, the instrument can be easily cleaned after use. The instrument may be assembled as follows. First, the holding member 2 is screwed onto the drive shaft 1 such that the first portion 14 of the drive shaft 1 extends through the holding member 2. The position of the holding member 2 on the drive shaft is limited in an axial direction by the abutment of the second end 22 of the holding member against the abutment surface 16a. Then, the displacement member 3 is connected to the actuator 4 such that the flap 36 is inserted into the actuator 4 until the projection 37 of the flap 36 rests on the shoulder 45a of the actuator 4 and the first end 41 of the actuator 4 rests on the free end surface 32a of the displacement member 3. Then, the pre-assembled displacement member 3 and actuator 4 are placed onto the drive shaft 1 from the second end 12 of the drive shaft 1, such that the internal threaded bore 43 of the actuator is screwed onto the externally threaded portion 18 of the drive shaft 1. Finally, the handle 5 is secured (e.g., clicked) onto the rear end section 19 of the drive shaft 1.

Figure 21:
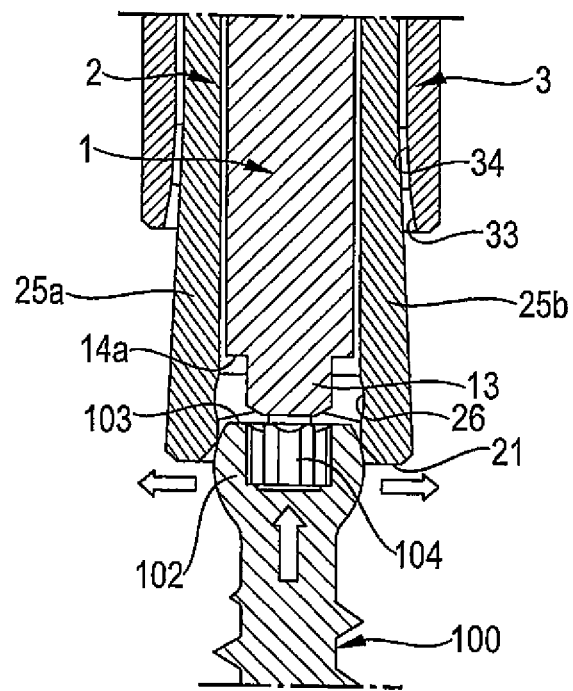
FIG. 21 shows a cross-sectional view of a portion of the instrument of FIGS. 1 to 6 in a first step of inserting a head of a bone anchor when the instrument is in the first configuration.
Figure 22:
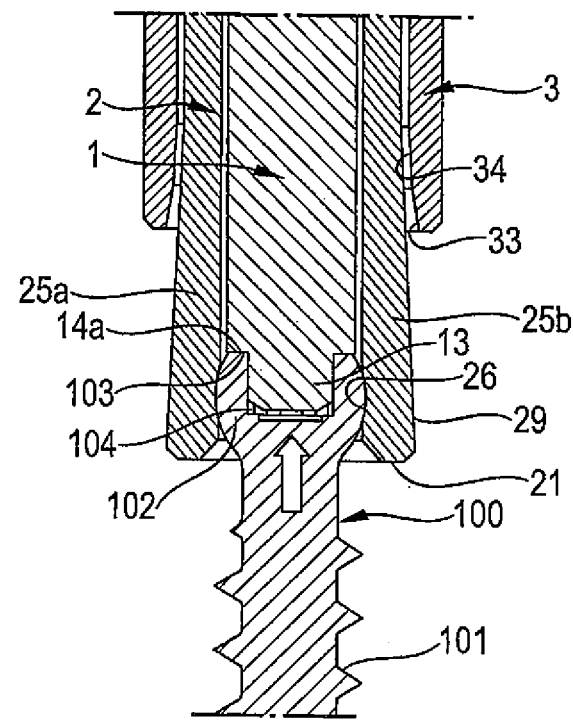
FIG. 22 shows a cross-sectional view of a portion of the instrument of FIGS. 1 to 6 in the first configuration with the head of the bone anchor inserted therein.

The use of the instrument with a bone anchor will be described with reference to FIGS. 21 to 23b. In the first configuration, the actuator 4 is in a first position closer to the second end 12 of the drive shaft 1 than it is in the second configuration. As shown in FIG. 2, to reach the first configuration, which is an "open configuration," the actuator 4 is rotated by a user's hands, for example in a counter clockwise direction. The displacement member 3 follows this movement and assumes a retracted position relative to the holding member 2 (e.g., the first end 31 of the displacement member 3 is retracted relative to the first end 21 of the holding member 2). The arms 25a, 25b of the holding member 2 project out of the displacement member 3 to such an extent that the arms 25a, 25b are configured to be resiliently spread apart from each other. As depicted in FIG. 21, in the first configuration, the head 102 pushes the two arms 25a, 25b away from each other until the head 102 snaps into the seat 26. During the insertion, the engagement projection 13 of the drive shaft enters into a corresponding engagement recess 104 provided at the free end surface 103 of the head 102. The engagement projection 13 can be inserted into the engagement recess 104 until the free end surface 103 of the head 102 abuts against the abutment surface 14a of the drive shaft 1. During this insertion step, the shank 101 is aligned with the drive shaft 1. The head 102 is held in a form-fit manner in the axial direction and also in the seat 26 such that the head 102 cannot be removed easily.

By rotating the actuator 4, for example, in a clockwise direction, the displacement member 3 is moved towards the first end 21 of the holding member 2 as depicted in FIG. 3. When the displacement member 3 moves towards the first end 21 of the holding member 2, the tapered inner surfaces 33, 34 of the displacement member 3 comes into contact with the outer tapered surface portion 29 of the holding member 2 as depicted in FIG. 23a. Thereby, the two arms 25a, 25b are pressed together. Simultaneously, the pressure is transmitted to the head 102, as depicted through the horizontal arrow $F_r$ in FIG. 23b. Because the center of the sphere $C_1$ of the spherical seat 26 is offset with respect to the center of the sphere $C_2$ of the head 102 in a direction towards the abutment surface 14a of the drive shaft 1, a force $F_\mu$ acts onto the head 102, with a component directed in an axial direction towards the abutment surface 14a. As a result thereof, the head 102 is firmly pressed onto the abutment surface 14a. Possible play between the engagement projection 13 and the engagement recess 104 is eliminated. Thereby, the surgeon can insert or implant the bone anchor 100 without any play.

In the above second configuration, which is a "closed configuration," the head 102 is firmly held in the holding member 2. In this configuration, the head 102 can be inserted into the bone. The first end 21 of the holding member 2 serves as an abutment for the bone that limits the insertion of the bone anchor 100 into the bone and ensures that a sufficient portion of the bone anchor projects over the bone surface, such that a receiving part can be later mounted onto the head 102.

An embodiment of a system or a kit can include the above described instrument and a bone anchor 100 having a head 102, wherein the seat 26 and the dimensions of the holding member 2 are adapted to the dimension of the head 102.

Various modifications of the above described embodiments are also possible.

Figure 24:
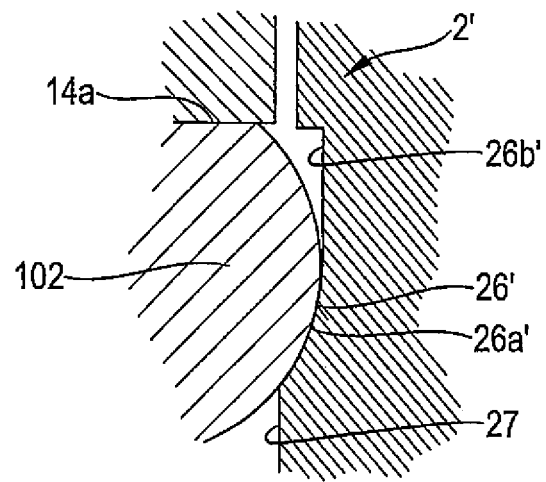
FIGS. 24 to 26 show schematic enlarged cross-sectional views of a lower portion of various modified embodiments of the instrument with a head of a bone anchor inserted therein.
Figure 25:
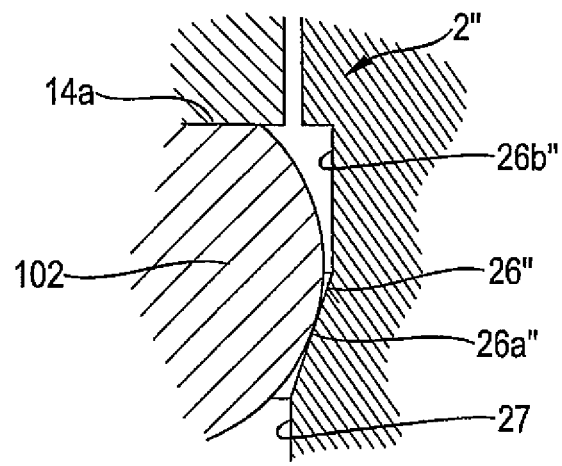
Figure 26:
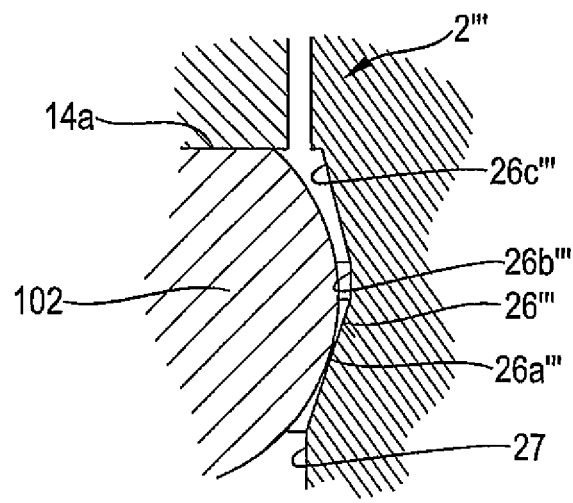

For example, referring to FIGS. 24 to 26, the seat 26 for the head 102 in the holding member 2 can have various different shapes. Parts and portions that are identical to the previously described embodiment are marked with the same reference signs, and the descriptions thereof will not be repeated. As depicted in FIG. 24, the holding member 2' may have a seat 26' that has a spherical segment shape 26a' adjacent to the lower cylindrical portion 27. The seat 26' also includes a slightly conically widening portion 26b' that widens in a direction towards the second or proximal end 22 of the holding member 2'. As in the previous embodiment, the size of the seat 26' is such that when the arms 25a, 25b are compressed, the head 102 experiences a force that presses the head 102 towards the abutment surface 14a.

In the embodiment shown in FIG. 25, the seat 26" has a lower tapered portion 26a" that tapers and narrows towards the first or distal end 21 of the holding member 2". The seat 26" also includes a cylindrical portion 26b" in a direction towards the second end 22 of the holding member 2". The inner diameter of the cylindrical portion 26b" is slightly larger than the largest diameter of the head 102. When the arms 25a, 25b are pressed together, the tapered portion 26a" exerts a force on the head 102 that urges or tries to move the head 102 upward towards the second end 22 of the holding member 2". Because of the abutment of the head 102 against the abutment surface 14a, the head 102 is firmly pressed against the abutment surface 14a.

In the embodiment shown in FIG. 26, the seat 26''' includes a first tapered portion 26a''' that is tapered and narrows towards the first end 21 of the holding member 2''', followed by a cylindrical portion 26b''', which is followed by a second tapered portion 26c''' that tapers and narrows towards the second end 22 of the holding member 2'''. The function of the seat 26a''' is the same or similar to the other embodiments.

In all embodiments, the seat 26, 26', 26", 26a''' has such a size that when the arms are compressed, the head 102 experiences a force that moves or urges the head 102 upward in the direction of the abutment surface 14a, whereby the head 102 is pressed against the abutment surface 14a.

In a further modified embodiment, the actuator can be realized by other means that facilitate the displacement of the displacement member between the first and the second configurations.

In some embodiments, the actuator can also be omitted. For example, the displacement member may have an internal thread that cooperates with an external thread of the holding member to facilitate advancement of the displacement member along the holding member.

In addition, the abutment surface need not to be circular or ring-shaped. Any abutment surface can be used that provides sufficient area to generate enough friction to eliminate play between the engagement projection of the drive shaft and the engagement recess of the head.

The holding member can have more than two arms, for example, three or more arms, that can be pressed together in a resilient manner.

Meanwhile, instead of the threaded connections shown in the embodiments, other detachable connections can also be provided.

For the bone anchor, any bone anchor can be used that has a shank and a head portion. It is not necessary that the bone anchor is a bone screw that has to be screwed in. For example, the instrument can also be suitable for pushing a bone anchor into a hole.

In addition, while the head of the bone anchor and the seat of the instrument are shown as being used in conjunction with a polyaxial bone anchor, it is also possible, for example, that the head and the seat have flat side portions that instead render the bone anchor suitable for a monoplanar bone anchoring device that allows pivoting only in a single plane.

While the present invention has been described in connection with certain embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A bone anchor and instrument system comprising:
   a bone anchor comprising a shank for anchoring to a bone and a head; and
   an instrument for holding and anchoring the bone anchor to the bone, the instrument comprising:
      a holding member for holding the head of the bone anchor, the holding member having a first end and an opposite second end, and comprising a plurality of arms configured to at least partially encompass the head of the bone anchor, wherein an inner surface of the arms forms a seat at the first end for the head; and
      a drive shaft configured to engage the head of the bone anchor and having an abutment surface for coupling to the head, wherein when the holding member and the drive shaft are assembled to one another, the drive shaft is positionable at least partially within the holding member and defines a longitudinal axis of the instrument, and the drive shaft is configured to directly engage another portion of the instrument that is spaced apart from the plurality of arms of the holding member to prevent the drive shaft from protruding out of the first end of the holding member;
   wherein the holding member is movable from a first configuration wherein the head is configured to contact and spread the arms to permit the head to enter the seat, to a second configuration wherein the head is held in the seat and the seat is provided at an axial position relative to the drive shaft such that the seat presses the head axially against the abutment surface of the drive shaft.

2. The system of claim 1, wherein the head has a spherical outer surface portion and the seat comprises a corresponding spherical inner surface portion.

3. The system of claim 2, wherein a region of a largest inner diameter of the spherical inner surface portion of the seat is situated between an edge of the seat closest to the first end of the holding member and an edge of the seat closest to the second end of the holding member.

4. The system of claim 2, wherein when the head is held in the seat, a center of the sphere that forms the spherical outer surface portion of the head is positionable between the first end of the holding member and a center of the sphere that forms the spherical inner surface portion of the seat.

5. The system of claim 1, wherein a first end of the drive shaft comprises an engagement projection configured to engage the head, and wherein the abutment surface is spaced apart from a free end of the engagement projection.

6. The system of claim 1, wherein the holding member comprises a first sleeve extending from the first end of the holding member with at least one slot such that the arms are formed by the slot and wherein the arms are resilient towards each other.

7. The system of claim 6, wherein the drive shaft is configured to extend through the first sleeve and is configured to be connected to the second end of the holding member.

8. The system of claim 6, further comprising a displacement member comprising a second sleeve configured to be arranged around at least a portion of the first sleeve and that is displaceable relative to the first sleeve in a direction along the longitudinal axis.

9. The system of claim 8, wherein the displacement member is configured to act on the holding member, and wherein the instrument further comprises an actuator for actuating the displacement member and for holding the displacement member relative to the holding member in the first configuration and in the second configuration.

10. The system of claim 9, wherein the actuator comprises a third sleeve connected to the drive shaft via a threaded connection.

11. The system of claim 9, wherein the displacement member is connectable to the actuator such that a movement of the actuator in a longitudinal direction displaces the displacement member in the longitudinal direction.

12. The system of claim 1, wherein the holding member is detachably connected to the drive shaft.

13. The system of claim 9, wherein the actuator is detachably connected to the drive shaft and is detachably connected to the displacement member.

14. The system of claim 1, further comprising a displacement member configured to be positioned at least partially around the holding member and configured to adjust the holding member from the first configuration to the second configuration.

15. The system of claim 1, wherein the displacement member is movable along the longitudinal axis relative to the holding member to exert a pressure force on the arms.

16. The system of claim 14, wherein the holding member directly engages the drive shaft and the displacement member directly engages the drive shaft.

17. The system of claim 1, wherein in the second configuration, a greatest diameter of the head is between the first end of the holding member and an axial position of the seat having a greatest distance between the arms.

18. A method of connecting an instrument to a bone anchor for holding and anchoring the bone anchor to a bone, the bone anchor comprising a shank for anchoring to the bone and a head, the instrument comprising a holding member for holding the head of the bone anchor, the holding member having a first end and an opposite second end, and comprising a plurality of arms configured to at least partially encompass the head of the bone anchor, wherein an inner surface of the arms forms a seat at the first end for the head, and a drive shaft configured to engage the head of the bone anchor and having an abutment surface for coupling to the head, wherein when the holding member and the drive shaft are assembled to one another, the drive shaft is positionable at least partially within the holding member and defines a longitudinal axis of the instrument, and the drive shaft is configured to directly engage another portion of the instrument that is spaced apart from the plurality of arms of the holding member to prevent the drive shaft from protruding out of the first end of the holding member, the method comprising:

contacting and spreading the arms with the head of the bone anchor to insert the head into the seat when the holding member is at a first configuration; and adjusting the holding member to a second configuration wherein the head is held in the seat, and wherein the seat is provided at an axial position relative to the drive shaft such that the seat presses the head axially against the abutment surface of the drive shaft.

19. A bone anchor and instrument system comprising:

a bone anchor comprising a shank for anchoring to a bone and a head having a spherical outer surface portion on a side of the head opposite the shank; and an instrument for holding and anchoring the bone anchor to the bone, the instrument comprising:

a holding member for holding the head of the bone anchor, the holding member comprising a plurality of arms configured to at least partially encompass the head of the bone anchor, wherein an inner surface of the arms forms a seat for the head; and a drive shaft configured to engage the head of the bone anchor and to be positioned at least partially within the holding member, the drive shaft defining a longitudinal axis of the instrument and having an abutment surface for coupling to the head;

wherein the holding member is movable from a first configuration wherein when the head is outside of the holding member, the spherical outer surface portion on the side of the head opposite the shank is configured to contact and spread the arms to permit the head to enter the seat, to a second configuration wherein the head is held in the seat and the seat is provided at an axial position relative to the drive shaft such that the seat presses the head axially against the abutment surface of the drive shaft.

20. The system of claim 19, wherein the seat comprises a spherical inner surface portion for engaging the spherical outer surface portion of the head.

21. The system of claim 1, wherein a second abutment between the drive shaft and the another portion of the instrument prevents the drive shaft from protruding out of the first end of the holding member.

* * * * *

UNITED STATES PATENT AND TRADEMARK OFFICE
CERTIFICATE OF CORRECTION

PATENT NO.        : 10,105,165 B2
APPLICATION NO.   : 14/645307
DATED             : October 23, 2018
INVENTOR(S)       : Lutz Biedermann et al.

Page 1 of 1

It is certified that error appears in the above-identified patent and that said Letters Patent is hereby corrected as shown below:

In the Claims
Column 11, Line 44, Claim 15         delete "claim 1," and insert -- claim 14, --

Signed and Sealed this
Nineteenth Day of November, 2019

Andrei Iancu
*Director of the United States Patent and Trademark Office*